(12) United States Patent
Modi et al.

(10) Patent No.: US 8,333,978 B2
(45) Date of Patent: Dec. 18, 2012

(54) POLY TLR ANTAGONIST

(75) Inventors: Indravadan Ambalal Modi, Ahmedabad (IN); Bakulesh Mafatlal Khamar, Ahmedabad (IN)

(73) Assignee: Cadila Pharmaceuticals, Ahmedabad (IN)

( * ) Notice: Subject to any disclaimer, the term of this patent is extended or adjusted under 35 U.S.C. 154(b) by 606 days.

(21) Appl. No.: 12/295,697

(22) PCT Filed: Nov. 21, 2007

(86) PCT No.: PCT/IB2007/003581
§ 371 (c)(1),
(2), (4) Date: Oct. 1, 2008

(87) PCT Pub. No.: WO2008/062288
PCT Pub. Date: May 29, 2008

(65) Prior Publication Data
US 2010/0062026 A1    Mar. 11, 2010

(30) Foreign Application Priority Data
Nov. 23, 2006   (IN) .......................... 1931/MUM/2006

(51) Int. Cl.
*A61K 39/04* (2006.01)
(52) U.S. Cl. .................................... 424/248.1
(58) Field of Classification Search ................ 424/248.1
See application file for complete search history.

(56) References Cited

U.S. PATENT DOCUMENTS
5,681,824 A    10/1997   Christ et al.
7,972,609 B2 *  7/2011   Khamar ...................... 424/248.1

FOREIGN PATENT DOCUMENTS
WO    WO/03049667    *  6/2003
WO    WO/03/075825   *  9/2003
WO    WO-2004071465     8/2004

OTHER PUBLICATIONS

Underhill et al Innate Immunity pp. 103-110.*
Medvedev et al Journal of Immunology pp. 2257-2267.*
Ellis 1999 Vaccine vol. 17 pp. 1596-1604.*
Ishi et al. (Current Pharmaceutical Design, 2006, vol. 12, No. 3).*
Bohnhorst et al 2006 Leukemia vol. 20 pp. 1138-1144.*
Togbe et al 2006 Society for Leukocyte Biology pp. 1-7.*
Underhill et al 2002 vol. 14 Innate Immunity pp. 103-110.*
Medvedev et al 2001 Journal of Immunology pp. 2257-2267.*
Branger et al 2004 International Immunology vol. 16 pp. 509-516).*
International Search Report for International Application No. PCT/IB2007/003581 mailed on Jul. 22, 2008.
International Preliminary Report on Patentability for International Application No. PCT/IB2007/003581 mailed on May 26, 2009.
Anders H.J. et al., "A Toll for lupus," *Lupus* vol. 14(6), (2005), p. 417-22.

Anders HJ, Zecher D, Pawar RD, Patole PS., "Molecular mechanisms of autoimmunity triggered by microbial infection," *Arthritis Res Ther*., vol. 7(5), (2005), p. 215-24.
Angus, Derek C., Linde-Zwirble, Walter T., Lidicker, Jeffrey, Clermont, Gilles,Carcillo, Joseph, Pinsky, Michael R., "Epidemiology of severe sepsis in the United States: Analysis of incidence, outcome, and associated costs of care," Critical Care Medicine. vol. 29(7), (2001), p. 1303-1310.
Ann Marshak-Rothstein, "Toll-like receptors in systemic autoimmune disease," *Nature Reviews Immunology*, vol. 6(11), (2006), p. 823-35.
Barrat, FJ. et al., "Nucleic acids of mammalian origin can act as endogenous ligands for Toll-like receptors and may promote systemic lupus erythematosus," *J Exp. Med.* vol. 202, (2005), p. 1131-1139.
Donald N Cook, David S Pisetsky & David A Schwartz, "Toll-like receptors in the pathogenesis of human disease," *Nature Immunology*, vol. 5(10), (2004), p. 975-979.
Emer Bourke, Daniela Bosisio, Jose'e Golay, Nadia Polentarutti, and Alberto Mantovani, "The toll-like receptor repertoire of human B lymphocytes: inducible and selective expression of TLR9 and TLR10 in normal and transformed cells," *Blood*. vol. 102, (2003), p. 956-963.
Foo Y. Liew, Damo Xu, Elizabeth K. Brint and Luke A. J. O'neil, "Negative Regulation of Toll Like Receptor Mediated Immune; Responses," *Nature Reviews Immunology* vol. 5,(2005), p. 446-458.
Fumiko Nomura, Sachiko Akashi, Yoshimitsu Sakao, Shintaro Sato, Taro Kawai, Makoto Matsumoto, Kenji Nakanishi, Masao Kimoto, Kensuke Miyake, Kiyoshi Takeda, and Shizuo Akira, "Endotoxin Tolerance in Mouse Peritoneal Macrophages Correlates with Down-Regulation of Surface Toll-Like Receptor 4 Expression1," *The Journal of Immunology*, vol. 164, (2000), p. 3476-3479.
G Jego, R Bataille, A Geffroy-Luseau, G Descamps, C Pellat-Deceunynck, "Pathogen-associated molecular patterns are growth and survival factors for human myeloma cells through Toll-like receptors," Leukemia 20, (2006), p. 1130-1137.
Gewirtz AT, Vijay-Kumar M, Brant SR, Duerr RH, Nicolae DL, Cho JH., "Dominant-negative TLR5 polymorphism reduces adaptive immune response to flagellin and negatively associates with Crohn's disease," Am J Physiol Gastrointest Liver Physiol. vol. 290(6), (2006), p. 1157-63.
Gilchrist M, Thorsson V, Li B, Rust AG, Korb M, Kennedy K, Hai T, Bolouri H, Aderem A., "Systems biology approaches identify ATF3 as a negative regulator of Toll-like receptor 4," Nature. vol. 441(7090), (2006), p. 173-8.

(Continued)

*Primary Examiner* — Gary Nickol
*Assistant Examiner* — Nina Archie
(74) *Attorney, Agent, or Firm* — Burns & Levinson LLP

(57) ABSTRACT

*Mycobacterium* w or its components are found to have poly TLR antagonistic activity to induced TLRs by varieties of TLR ligands. The induced TLR against which inhibitory effect is seen includes TLR 3, 4, 5, 6, 7, 8, 9. They also display antagonistic activities to effects of TLR ligands. They are also useful in management of diseases wherein TLRs are over expressed, like sepsis, multiple sclerosis, optic neuritis, Chronic obstructive pulmonary diseases multiple myeloma etc.

7 Claims, 6 Drawing Sheets

OTHER PUBLICATIONS

Gowen BB, Hoopes JD, Wong MH, Jung KH, Isakson KC, Alexopoulou L, Flavell RA, Sidwell RW, "TLR3 deletion limits mortality and disease severity due to Phlebovirus infection," J Immunol. vol. 177(9), (2006), p. 6301-7.

Ishii Ken et al, "Toll gates for future immunotherapy," Current pharmaceuticals design, vol. 12, (2006), p. 4135-4142.

J Bohnhorst, T Rasmussen, S H Moen, M Fiã, ttum, L Knudsen, M Bã, rset, T Espevik, A Sundan, "Toll-like receptors mediate proliferation and survival of multiple myeloma cells," Leukemia vol. 20, (2006), p. 1138-1144.

Julianne Stack, Ismar R. Haga, Martina Schroder, Nathan W. Bartlett, Geraldine Maloney, Patrick C. Reading, Katherine A. Fitzgerald, Geoffrey L. Smith, and Andrew G. Bowie, "Vaccinia virus protein A46R targets multiple Toll-like-interleukin-I receptor adaptors and contributes to virulence," J Exp. Med. vol. 201(6), (2005), p. 1007-1018.

Leadbetter, E. A., Rifkin, I. R., Hohlbaum, A. M., Beaudette, B. C., Shlomchik, M. J., Marshak-Rothstein, A., "Chromatin-IgG complexes activate B cells by dual engagement of IgM and Toll-like receptors," *Nature*, vol. 416, (2002), p. 603-607.

Lene Malmgaard, Jesper Melchjorseri, Andrew G. Bowie, SØren C. Mogensen, and SØren R. Paludan, "Viral Activation of Macrophages through TLR-Dependent and Independent Pathways1," The Journal of Immunology, vol. 173, (2004), p. 6890-6898.

Lenert PS et al., "Targeting Toll-like receptor signaling in plasmacytoid dendritic cells and autoreactive B cells as a therapy for lupus." Arthritis Res Ther. vol. 8(1), (2006), p. 203.

Maureen, Mullarkey, Jeffrey R. Rose, John Bristol, Tsutomu Kawata, Akufumi Kimura, Seiichi Kobayashi, Melinda Przetak, Jesse Chow, Fabian Gusovsky, William J. Christ and Daniel P. Rossignol, "Inhibition of Endotoxin Response by E5564, a Novel Toll-Like Receptor 4 Directed Endotoxin Antagonist," J Pharmacal Exp. Thera., vol. 304(3), (2003), p. 1093-1102.

Papadimitraki ED, Choulaki C, Koutala E, Bertsias G, Tsatsanis C, Gergianaki I, Raptopoulou A, Kritikos HD, Mamalaki C, Sidiropoulos P, Boumpas DT, "Expansion of toll-like receptor 9-expressing B cells in active systemic lupus erythematosus: implications for induction and maintenance of the autoimmune process," Arthritis Rheum. vol. 54(11), (2006), p. 3601-11.

RC Bone, RA Balk, FB Cerra, RP Dellinger, AM Fein, WA Knaus, RM Schein, and WJ Sibbald, "Definitions for sepsis and organ failure and guidelines for the use of innovative therapies in sepsis," Chest vol. 101, (1992), p. 1644-55.

Rossignol, D.P. & Lynn, M. TLR4 antagonists for endotoxemia and beyond, "TLR4 antagonist eritoran (E5564) and TAK-242 are found useful in management of sepsis," Curr. Opin. Investig. Drugs vol. 6, (2005), p. 496-502.

Ruslan Medzhitov, Paula Preston-Huriburt and Charles A. Janeway, Jr, "A human homologue of the *Drosophila* Toll protein signals activation of adaptive immunity," Nature vol. 388, (1997), p. 394-397.

Subramanian S, Tus K, Li QZ, Wang A, Tian XH, Zhou J, Liang C, Bartov G, McDaniel LD, Zhou XJ, Schultz RA, Wakeland EK, "A TLR7 translocation accelerates systemic autoimmunity in murine lupus," Proc Natl Acad Sci USA. vol. 103(26), (2006), p. 9970-5.

Sukkar MB, Xie S, Khorasani NM, Kon OM, Stanbridge R, Issa R, Chung KF, "Toll-like receptor 2, 3, and 4 expression and function in human airway smooth muscle," J Allergy Clin Immunol. vol. 18(3), (2006), p. 1641-8.

Togbe D, Schnyder-Candrian S, Schnyder B, Couillin I, Maillet I, Bihl F, Malo D, Ryffel B, Quesniaux VF, "TLR4 gene dosage contributes to endotoxin-induced acute respiratory inflammation," J Leukoc Biol. Vol; 80(3), (2006), p. 451-7.

Toiyama Y, Araki T, Yoshiyama S, Hiro J, Miki C, Kusunoki M., "The expression patterns of Toll-like receptors in the ileal pouch mucosa of postoperative ulcerative colitis patients," Surg. Today. vol. 36(3), (2006), p. 287-90.

Wang T, Town T, Alexopoulou L, Anderson JF, Fikrig E, Flavell RA, "Toll-like receptor 3 mediates West Nile virus entry into the brain causing lethal encephalitis," *Nat Med.* vol. 10(12), (2004), p. 1366-73.

Wei Jiang, Rui Sun, Haiming Wei, and Zhigang Tian, "Toll-like receptor 3 ligand attenuates LPS-induced liver injury by down-regulation of toll-like receptor 4 expression on macrophages," *PNAS*, vol. 102(47), (2005), p. 17077-17082.

Xiong J, Zhu ZH, Liu JS, Wang Y, Wu HS., "The expression of toll-like receptor 2,4 of livers in mice with systemic inflammatory response syndrome," *HepatobillaTJI Pancreat Dis Int.* vol. 5(1), (2006), p. 143-6.

Akira Shimamoto, Albert 1. Chong, Masaki Yada, Shin Shomura, Hiroo Takayama, Ani J.Fleisig, Matthew L. Agnew, Craig R. Hampton, Christine L. Rothnie, Denise 1. Spring, Timothy H. Pohlman, Hideto Shimpo, and Edward D. Verrier, "Inhibition of Toll-like Receptor 4 With Eritoran Attenuates Myocardial Ischemia-Reperfusion Injury," Circulation, vol. 114, (2006), I-270-I-274.

Shizuo Akira and Kiyoshi Takeda, "Toll-Like Receptor signaling," Nature Reviews Immunology vol. 4, (2004), p. 499.

* cited by examiner

Figure 04

I. E. coli

II. E. coli + Dexamethasone (0.5 mL of 4 mg/mL)

III. E. coli + Amoxicillin (500 mg/Kg)

IV. E. coli + Dexamethasone + Amoxicillin + Mycobacterium w 0.1 mL ID

V. E. coli + Dexamethasone + Amoxicillin + Mycobacterium w 0. 1 mL IV

VI. E. coli + Dexamethasone + Mycobacterium w 0.1 mL ID

VII. E. coli + Dexamethasone + Mycobacterium w0.1 mL IV

Figure 05

I. E. coli

II. E. coli + Dexamethasone (2.0 mg) + Amoxicillin (70 mg/KG) + Mycobacterium w 0.1 mL ID III. E. coli + Dexamethasone (2.0 mg) + Amoxicillin (70 mg/KG) + Mycobacterium w 0. 1 mL IV IV. E. coli + Amoxicillin (70 mg/KG) + Mycobacterium w 0.1 mL ID V. E. coli + Amoxicillin (70 mg/KG) + Mycobacterium w0.1 ml IV

Figure 06

I. E. coli

II. E. coli + Dexamethasone (0.5 mg/kg)

III. E. coli + Dexamethasone (0.5 mg/kg) + Mycobacterium w 0.1ml ID

IV. E. coli + Amoxicillin (70 mg/KG)

V. E. coli + Dexamethasone (0.5 mg/kg) + Amoxicillin (70 mg/KG)

VI. E. coli + Dexamethasone (0.5 mg/kg) + Amoxicillin (70 mg/KG) + Mycobacterium w 0.1ml ID

POLY TLR ANTAGONIST

CROSS REFERENCE TO RELATED APPLICATIONS

This is a U.S. National Phase Application under 35 U.S.C. §371 of International Patent Application No. PCT/IB2007/003581 filed Nov. 21, 2007 which claims priority to Indian Patent Application No. 1931/MUM/2006 filed Nov. 23, 2006. The International Application was published in English on May 29, 2008 as WO 2008/062288 A2 under PCT Article 21(2).

FIELD OF INVENTION

The present invention provides means of reducing induced TLR activity using *Mycobacterium* w or its components and management of diseases associated with TLR antagonists using *Mycobacterium* w or its components.

BACKGROUND OF THE INVENTION

The present invention provides poly-toll like receptor antagonist (TLR). The tolls like receptors (TLR) are family of proteins. The innate immune system recognizes pathogens and initiates an effective and appropriate response through TLRs. TLRs are part of the larger IL-IR/TLR super family, which includes IL-IRs, IL-18Rs, and a group of orphan receptors. The family is defined by the presence of a cytoplasmic Toll-like-IL-1 resistance (TIR) domain, which is responsible for mediating downstream signaling. So far, 13 TLRs have been identified; TLRs 1-9 are common to mouse and human, whereas TLR10 is only functional in humans, and TLRs 11, 12, and 13 have been found only in mice. Many but not all of these receptors have been assigned a role in the initial detection of, and response to, specific pathogen-associated molecules (PAMs).

In macrophages and neutrophils, this drives innate immune responses, such as inflammation and induction of microbicidal activity, whereas activation of TLRs expressed on dendritic cells leads to the initiation of adaptive immunity through induction of IL-12 and co-stimulatory molecules.

Though TLRs are part of protective system of the body, their over expression is associated with variety of diseases. Sepsis is one of such disease. The incidence of sepsis due to infection in the United States has been estimated to be approximately 750,000 cases per year, with a mean mortality rate of about 30% (Angus et al., *Crit. Care Med*. Vol. 29, (2001), p 1303-1310). Endotoxin, or lipo-polysaccharide (LPS), which is a major component of the cell wall of gram-negative bacteria, is the causative agent of gram-negative sepsis. Endotoxin induces an innate immune response mainly through toll-like receptor 4 (TLR4) (Medzhitov et al., *Nature* Vol. 388(6640), (1997), p 394-397) in infected hosts, by which the body is warned of the bacterial infection, thus leading to an antimicrobial attack by the host immune system.

Such an immune response is usually beneficial to infected hosts, however, an overwhelming immune response to endotoxin can be pathological, leading to systemic inflammatory response syndrome (SIRS), organ failure, several sepsis and, possibly, septic shock and death. The symptoms of these conditions include fever, generalized inflammation, and more severe conditions, such as disseminated intravascular coagulation (DIC), hypotension, acute renal failure, acute respiratory distress syndrome (ARDS), hepatocellular destruction, and cardiac failure.

Toll like receptors expressed by LPS include TLR 2, 9, others besides TLR4. While endotoxin itself is a highly heterogeneous molecule, the expression of many of the toxic properties of endotoxin is attributed to the highly conserved hydrophobic lipid A portion. An effective drug that acts as a TLR4 antagonist, and which is an antagonist to this conserved structure of Lipid A, is known as E5564 (also known as compound 1287, SGEA, and Eriforan) (Mullarkey et al., *J. Pharmacol. Exp. Ther.* 304 (3): 1093-1102, 2003). This drug is described as compound 1 in U.S. Pat. No. 5,681,824, WO/2004/071465 (Methods and kits for use in the diagnosis and treatment of endotoxemia) describes A method of determining whether a patient could benefit or continue to benefit from treatment with a toll-like receptor 4 (TLR4) antagonist. It is also known that inhibition of Toll-like receptor 4 with eritoran attenuates myocardial ischemia-reperfusion injury. *Circulation* 114(1 Suppl), (2006), p 1270-4

The other diseases wherein one or more TLRs are over expressed include but not limited to following, 1. Exacerbation of latent or active viral infections (e.g., infection with HIV, cytomegaloviruses, herpes simplex, and influenza virus),
2. Inborn or acquired predisposition to pulmonary bacterial infection,
3. Congestive heart failure with pulmonary edema.
4. Chronic obstructive pulmonary disease
5. multiple myeloma
6. SLE.
7. Lupus
8. Ulcerative colitis
9. Crohn's disease
10. Autoimmune diseases
11. Rheumatoid diseases
12. Chronic hepatitis
13. Malaria (*P. Falciparum*)
14. Multiple sclerosis
15. Optic neuritis.
16. Viral encephalitis (West Nile)
17. Candidiasis
18. Atherosclerosis Some of these disorders are amenable to conventional therapy while there is no definitive therapy for majority of the diseases.

Selected antibacterial, anti-inflammatory, and immunomodulating adjunctive therapies investigated in patients with severe sepsis and septic shock.

| Type of therapy | Target (s) | Agents |
|---|---|---|
| Neutralisation of microbial toxins | Endotoxin | Anti-endotoxin antibodies, anti-lipid A antibodies, lipopolysaccharide analogues, lipopolysaccharide removal |

-continued

| Type of therapy | Target (s) | Agents |
| --- | --- | --- |
| Non-specific anti-inflammatory and immunomodulating drugs | Multiple inflammatory and immune mediators | High dose corticosteroids, low dose corticosteroids, pentoxifylline, immunoglobulins, interferon gamma |
| Inhibition of specific Mediators | Pro-inflammatory cytokines: Tumour necrosis Factor | Anti-tumour necrosis factor antibodies, soluble tumour necrosis factor receptors |
| | Interleukin-1 Phospholipid components: | Interleukin-1 receptor antagonist |
| | Phospholipase A2 | Phospholipase A2 inhibitor |
| | Cyclo-oxygenase | Ibuprofen |
| | Thromboxane | Dazoxiben, ketoconazole |
| | Platelet activating factor | Platelet activating factor antagonists platelet activating factor acetylhydrolase |
| | Oxygen free radicals | N-acetylcysteine, selenium |
| | Nitric oxide | N-methyl-L-arginine |
| | Bradykinin | Bradykinin antagonist |
| Correction of Coagulation cascade coagulopathy | Antithrombin III, tissue factor pathway inhibitor, | activated protein C |

In spite of all these morbidity associated with sepsis has not reduced. Thus there is a need to provide better therapeutic options for such diseases.

*Mycobacterium* w is a non-pathogenic, cultivable, atypical mycobacterium, with biochemical properties and fast growth characteristics resembling those belonging to Runyons group IV class of *Mycobacteria*. It has been found to share antigens with *Mycobacterium leprae* and *Mycobacterium tuberculosis*. It is found to provide prophylaxis against leprosy in humans by converting lepromin negative individuals to lepromin positivity. It is also found to provide prophylaxis against tuberculosis in animals. In leprosy it is also found to reduce duration of therapy for bacterial killing, clearance as well as clinical cure when used along with multi drug therapy. The pharmaceutical composition containing *Mycobacterium* W is approved for human use since 1998 in India.

This has been described in various patents and publications. Heat killed mycobacterium w is available as a commercial preparation in India. It contain $0.5 \times 10^9$ cells heat killed of *Mycobacterium* W per 0.1 ml of pharmaceutical composition.

OBJECT OF INVENTION

The object of the invention is to reduce induced TLR activity using *Mycobacterium* w or its components.

Another object of invention is to provide poly TLR antagonist activity of mycobacterium or its components when induced by known TLR agonist synthetic like CPG, ODN or naturally occurring like lipo-polysaccharide.

Another object of invention is to provide antagonists activity of *mycobacterium* w and its components to effects of TLR ligands like lipo-polysaccharide, *E-coli* etc.

Another object of invention is to provide usefulness of *Mycobacterium* w or its components in management of diseases where in TLRs are over expressed.

Another object of invention is to provide *Mycobacterium* w or its components in management of disease like sepsis, multiple myeloma, malaria, multiple sclerosis, optic neuritis, chronic obstructive pulmonary disease to improve morbidity and mortality associated them.

DETAILED DESCRIPTION OF THE INVENTION

Figure 1:
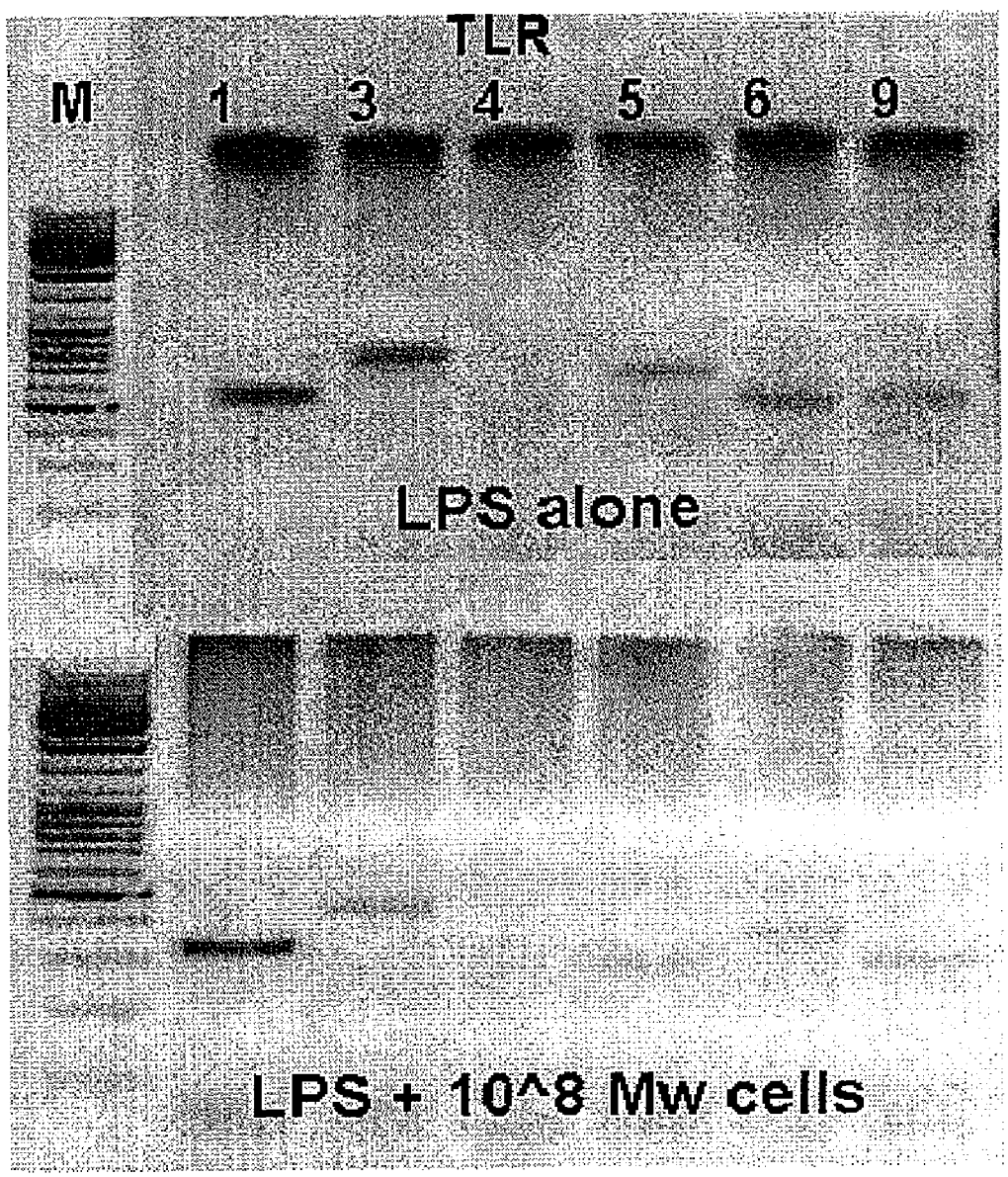
FIG. 1 Effect of *Mycobacterium* w on LPS induced TLRs
FIG. 2 Effect of *Mycobacterium* w on poly TLR ligand in induced TLRs
FIG. 3 Effect of *Mycobacterium* w on LPS ligand in induced pyrexia (Pyrogen test)
FIG. 4 Effect of *Mycobacterium* w containing composition on Sepsis induced by *E. coli* (Intra peritoneal+high'dose antibiotic)
FIG. 5 Effect of *Mycobacterium* w containing composition on Sepsis induced by *E. coli* (Intra Peritoneal+Low Dose Antibiotic)
FIG. 6 Effect of *Mycobacterium* w containing composition on sepsis induced by *E. coli* (Intravenous)

Pharmaceutical compositions containing *Mycobacterium* w and/or its components are known to provide Th1 response. They are also known to share antigens with *Mycobacterium Leprac* and *Mycobacterium tuberculosis*. They are found useful in management of Leprosy to improve killing of organisms and clearance of them of body resulting in faster cure. They have been found useful as a prophylaxis against tuberculosis and leprosy also.

Surprisingly it is observed that they also possess unique properties of reducing TLR activity. Their inhibitory/antagonist effect is seen at least agonist TLR 3, 4, 5, 6, 9. The reduction in TLR activity is observed when TLRs are expressed through variety of TLR ligands in vitro as well as in vivo. It is also found useful in management of conditions induced by TLR ligands like lipopolysaccharides e.g. (cytokines and pyroxia). It is also found useful in management of diseases where in various toll like receptors are over expressed e.g. sepsis, multiple myeloma, malaria, multiple sclerosis, optic neuritis, chronic obstructive pulmonary disease etc.

The invention is illustrated by way of following examples without limiting the scope of invention.

I. In accordance with the invention the composition of a pharmaceutical composition the method of preparation, HPLC characteristic its safety and tolerability, methods of use and outcome of treatments are described in following examples. The following are illustrative examples of the present invention and scope of the present invention should not be limited by them.

EXAMPLE 1

The pharmaceutical compositions

A. Each dose of 0.1 ml of therapeutic agent contains:

| | |
|---|---|
| *Mycobacterium* w., (heat killed) | $0.50 \times 10^9$ |
| Sodium Chloride I.P. | 0.90% w/v |
| Tween 80 | 0.1% w/v |
| Thiomerosal I.P. | 0.01% w/v (As a Preservative) |
| Water for injection I.P. | q.s. to 0.1 ml |

B. Each dose of 0.1 ml of therapeutic agent contains:

| | |
|---|---|
| *Mycobacterium* w., (heat killed) | $0.50 \times 10^9$ |
| Sodium Chloride I.P. | 0.90% w/v |
| Triton × 100 | 0.1% w/v |
| Thiomerosal I.P. | 0.01% w/v (As a Preservative) |
| Water for injection I.P. | q.s. to 0.1 ml |

C. Each dose of 0.1 ml of therapeutic agent contains:

| | |
|---|---|
| *Mycobacterium* w., (heat killed) | $0.50 \times 10^9$ |
| Sodium Chloride I.P. | 0.90% w/v |
| Thiomerosal I.P. | 0.01% w/v (As a Preservative) |
| Water for injection I.P. | q.s. to 0.1 ml |

D. Each dose of 0.1 ml of therapeutic agent contains

| | |
|---|---|
| Extract of Mycobacterium w after sonication from $1 \times 10^{10}$ Mycobacterium w | |
| Sodium Chloride I.P. | 0.90% w/v |
| Thiomerosal I.P. | 0.01% w/v (As a Preservative) |
| Water for injection I.P. | q.s. to 0.1 ml |

E. Each dose of 0.1 ml of therapeutic agent contains Methanol Extract of $1 \times 10^{10}$ *Mycobacterium* w

| | |
|---|---|
| Sodium Chloride I.P. | 0.90% w/v |
| Thiomerosal I.P. | 0.01% w/v (As a Preservative) |
| Water for injection I.P. | q.s. to 0.1 ml |

F. Each dose of 0.1 ml of therapeutic agent contains Chloroform Extract of $1 \times 10^{10}$ *Mycobacterium* w

| | |
|---|---|
| Sodium Chloride I.P. | 0.90% w/v |
| Thiomerosal I.P. | 0.01% w/v (As a Preservative) |
| Water for injection I.P. | q.s. to 0.1 ml |

G. Each dose of 0.1 ml of therapeutic agent contains Acetone Extract of $1 \times 10^{10}$ *Mycobacterium* w

| | |
|---|---|
| Sodium Chloride I.P. | 0.90% w/v |
| Thiomerosal I.P. | 0.01% w/v (As a Preservative) |
| Water for injection I.P. | q.s. to 0.1 ml |

H. Each dose of 0.1 ml of therapeutic agent contains Ethanol Extract of $1 \times 10^{10}$ *Mycobacterium* w

| | |
|---|---|
| Sodium Chloride I.P. | 0.90% w/v |
| Thiomerosal I.P. | 0.01% w/v (As a Preservative) |
| Water for injection I.P. | q.s. to 0.1 ml |

I. Each dose of 0.1 ml of therapeutic agent contains Liticase Extract of $1 \times 10^{10}$ *Mycobacterium* w

| | |
|---|---|
| Sodium Chloride I.P. | 0.90% w/v |
| Thiomerosal I.P. | 0.01% w/v (As a Preservative) |
| Water for injection I.P. | q.s. to 0.1 ml |

J. Each dose of 0.1 ml of therapeutic agent contains *Mycobacterium* w (heat killed) $0.5 \times 10^7$
Extract of *mycobacterium* w obtained $1 \times 10^3$ *Mycobacterium* w by disruption, solvent extraction or enzymatic extraction.

| | |
|---|---|
| Sodium Chloride I.P. | 0.90% w/v |
| Thiomerosal I.P. | 0.01% w/v (As a Preservative) |
| Water for injection I.P. | q.s. to 0.1 ml |

EXAMPLE 2

The Process of Preparing a Pharmaceutical Composition

A. Culturing of *Mycobacterium* w.

i) Preparation of Culture Medium.

*Mycobacterium* w is cultured on solid medium like L J medium or liquid medium like middle brook medium or sauton's liquid medium.

For better yield middle brook medium is enriched. It can be preferably enriched by addition of glucose, bactotryptone, and BSA. They are used in ratio of 20:30:2 preferably. The enrichment medium is added to middle brook medium. It is done preferably in ratio of 15:1 to 25:1 more preferably in ratio of 20:1.

ii) Bioreactor Operation a) Preparation of Vessel:

The inner contact parts of the vessel (Joints, mechanical seals, o-ring/gasket grooves, etc.) should be properly cleaned to avoid any contamination. Fill up the vessel with 0.1 N NaOH and leave as such for 24H to remove pyrogenic materials and other contaminants. The vessel is then cleaned first with acidified water, then with ordinary water. Finally, the vessel is rinsed with distilled water (3 times) before preparing medium.

b) Sterilization of Bioreactor

The bioreactor containing 9 L distilled water is sterilized with live steam(indirect). Similarly the bioreactor is sterilized once more with Middlebrook medium. The other addition bottles, inlet/outlet air filters etc. are autoclaved (twice) at 121° C. for 15 minutes. Before use, these are dried at 50° C. oven.

c) Environmental Parameter i. Temperature: 17±0.5° C.

ii. pH: 6.7 to 6.8 initially.

B. Harvesting and Concentrating
It is typically done at the end of $6^{th}$ day after culturing under aseptic condition. The concentration of cells (palletisation) is done by centrifugation.

C. Washing of Cells
The pallet so obtained is washed minimum three times with normal saline. It can be washed with any other fluid which is preferably isotonic.

D. Adding Pharmaceutically Acceptable Carrier.
Pyrogen free normal saline is added to pallet. Any other pyrogen free isotonic fluid can be used as a pharmaceutical carrier. The carrier is added in amount so as get to desired concentration of active in final form.

E. Adding Preservative
To keep the product free from other contaminating bacteria for its self life preservative is added. Preferred preservative is thiomesol which is used in final concentration of 0.01% w/v.

F. Terminal Sterilization
Terminal sterilization can do by various physical methods like application of heat or ionizing radiation or sterile filtration.
Heat can be in the form of dry heat or moist heat. It can also be in the form of boiling or pasturisation. Ionizing radiation can be ultraviolet or gamma rays or microwave or any other form of ionizing radiation. It is preferable to autoclave the final product.
This can be done before after filling in a final packaging.

G. Quality Control
i. The material is evaluated for purity, sterility.
ii. The organisms are checked for acid fastness after gram staining.
iii. Inactivation test: This is done by culturing the product on L 0.1 medium to find out any living organism.
iv. Pathogenicity and/or contamination with pathogen.
The cultured organisms are infected to Balb/c mice.
None of the mice should die and all should remain healthy and gain weight.
There should not be any macroscopic or microscopic lesions seen in liver, lung spleen or any other organs when animals are killed up to 8 weeks following treatment.
v. Biochemical Test:
The organism is subjected to following biochemical tests:
a) Urease
b) Tween 80 hydrolysis
c) Niacin test
d) Nitrate reduction test
The organism gives negative results in urease, tween 80 hydrolysis and niacin test. It is positive by nitrate reduction test.

H. Preparation of Constituents of *Mycobacterium* w.
The constituents of *Mycobacterium* w can be prepared for the purpose of invention by:
I. Cell disruption
II. Solvent extraction
III. Enzymatic extraction.
The cell disruption can be done by way of sonication or use of high pressure fractionometer or by application of osmotic pressure ingredient.
The solvent extraction can be done by any organic solvent like chloroform, ethanol, methanol, acetone, phenol, isopropyl alcohol, acetic acid, urea, hexane etc.
The enzymatic extraction can be done by enzymes which can digest cell wall/membranes. They are typically proteolytic in nature. Enzyme liticase and pronase are the preferred enzymes. For the purpose of invention cell constituents of *Mycobacterium* w can be used alone in place of *mycobacterium* w organisms or it can be added to the product containing *mycobacterium* w.
Addition cell constituents results in improved efficacy of the product.
In all examples *Mycobacterium* w used is as described in example 1 c which contains heat killed *Mycobacterium* w $0.50 \times 10^9$ per 0.1 ml.

II. Examples demonstrating reduction in induced TLR using pharmaceutical compositions of present invention.

EXAMPLE 1

TLR stimulation is tested by assessing NF-κβ activation in HEK293 cells expressing a given TLR. The antagonistic activity of pharmaceutical composition containing $0.5 \times 10^9$ cells of heat killed *mycobacterium* w in 0.1 ml normal saline is tested on human TLR: 2, 3, 4, 5, 7, 8 and 9.

TLR ligands used in the study:
hTLR2: HKLM (heat-killed *Listeria monocytogenes*) at and $2 \times 10^7$, $1 \times 10^7$, $2 \times 10^6$ and $1 \times 10^6$ cells/ml
hTLR3: Poly (I:C) at 20 and 10 ng/ml
hTLR4: *E. coli* K12 LPS at 2 and 1 ng/ml
hTLR5: *S. typhimurium* flagellin at 20 and 10 ng/ml
hTLR7: Loxoribine at 1 and 0.5 mM
hTLR8: ssRNA40 at 5 and 3 μg/mL
hTLR9: CpG ODN 2006 at 50 and 20 ng/ml General Procedure
The secreted alkaline phosphatase reporter is under the control of a promoter inducible by the transcription factor NF-κB. TLR stimulation in the screening is tested by assessing NF-κB activation in the HEK293 cells expressing a given TLR. This reporter gene allows the monitoring of signaling through the TLR, based on the activation of NF-κB. In a 96-well plate (200 μL total volume) containing the appropriate HEK293 cells (25,000-50,000 cells/well), we add 20 μL of heat killed *Mycobacterium* was well as the TLR ligands to the wells. The media added to the wells is designed for the detection of NF-κB induced SEAP expression. After a 16-20 hr incubation to find out induced NF-κB activity by OD at 650 nm on a Beckman Coulter AD 340C Absorbance Detector is read.

The results are provided in tabular form as mentioned below. Column (A) demonstrate activity induced by TLR ligands. Column (B) demonstrates activity induced by TLR ligand in presence of *Mycobacterium* w (Mw) containing composition. The last column provides % antagonism induced by *Mycobacterium* w in relation to TLR ligand alone.

| TLR | POSITIVE CONTROL (TLR Ligand) (A) | POSITIVE CONTROL + Mw (B) | B/A % | Antagonism % |
|---|---|---|---|---|
| TLR3 | 1.881 | 1.445 | 76.8% | 23.2% |
| TLR4 | 1.207 | 0.602 | 49.87% | 50.13% |
| TLR5 | 2.227 | 1.134 | 50.92% | 49.08% |
| TLR7 | 1.503 | 1.141 | 74.57% | 25.43% |
| TLR8 | 0.591 | 0.431 | 72.92% | 27.08% |
| TLR9 | 1.979 | 0.135 | 0.07% | 99.93% |
| TLR2 | 2.21 | 2.17 | 98.19% | 1.81% |

The findings are suggestive of TLR antagonism when stimulated by a TLR ligand for TLR 3, 4, 5, 7, 8, 9. The antagonism is not seen for TLR2 in this experiment.

EXAMPLE 2

Mice of 8-10 weeks were sacrificed and spleenocytes were isolated from spleen. The spleen cells were cultured with different concentrations of LPS and combination of LPS with *Mycobacterium* w heat killed cells. The Cells were cultured in RPMI 1640 media.

After 48 hrs the cells are harvested and checked for expression of different TLRs. The TLR expression is checked by amplifying the specific mRNA from the cell lysate (Cell-cDNA H kit, Ambion) using TLR specific primers (R & D systems).

The amplified products are checked on 1.5% agarose gel using Ethidium Bromide staining.

It has been observed that expression of TLR3, 4, 5, 6 and 9 is reduced when cells are exposed to *Mycobacterium* w+LPS in comparison to LPS alone. There is no effect seen on TLR1. (FIG. 1). Thus *Mycobacterium* w containing pharmaceutical composition demonstrates antagonist activity to LPS induced induction of TLR 3, 4, 5, 6 and 9. It has no effect on LPS induced TLR1

EXAMPLE 3

Administration of a poly TLR ligand to mice results in expression of TLR 1, 3, 5, 6, 9 in splenocyte. When harvested and analyzed 7 days later.

Figure 2:
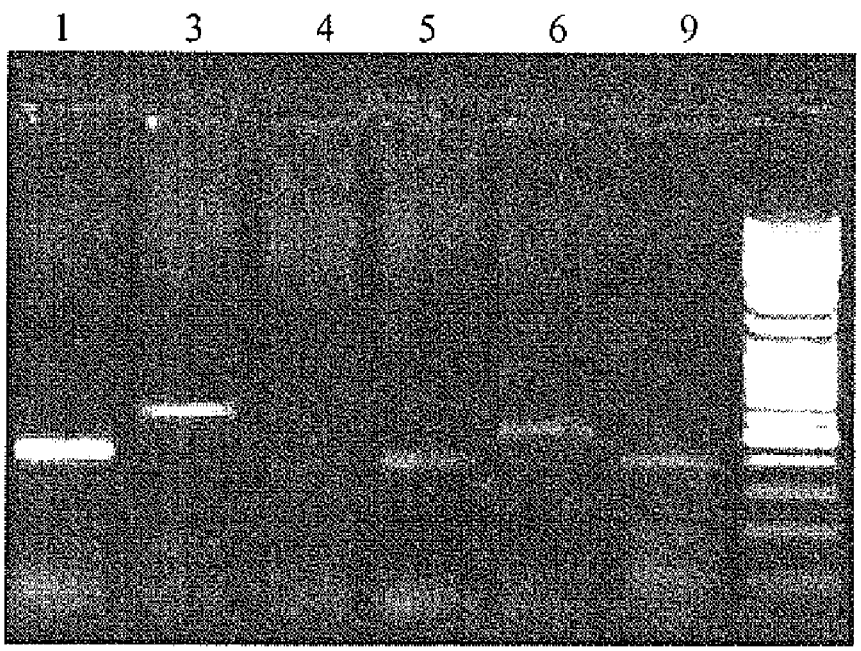
Figure 2:
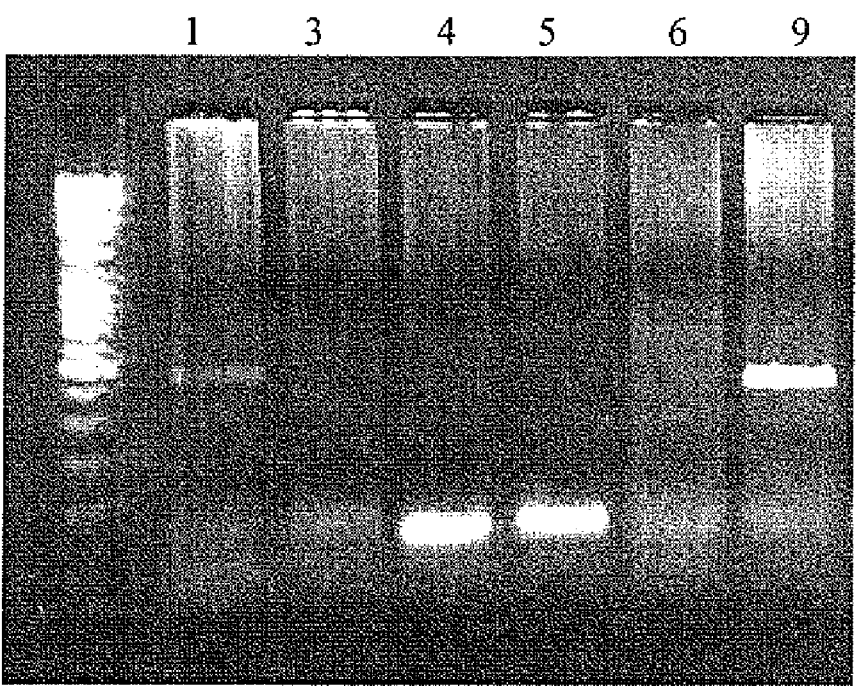

Splenocytes expressing TLR 1, 3, 5, 6, 9 when stimulated in vitro for 48 hrs with $0.5 \times 10^5$ or more of heat killed *mycobacterium* w, it results in absence of expression of TLR 3, 5 and 6. (100% reduction in expression of TLR 3, 5 and 6) The results are demonstrated in FIG. 2.

Thus above examples demonstrate reduction in induced TLRs by pharmaceutical composition of present invention.

III. Examples Demonstrating Antagonistic Activity to Effect of TLR Ligands.

EXAMPLE 1

Effect on LPS Induced Cytokines

Mice of 8-10 weeks were sacrificed and spleenocytes were isolated from spleen. The spleen cells were cultured with different concentrations of LPS and combination of LPS with *Mycobacterium* w heat killed cells. The Cells were cultured in RPMI 1640 media.

Superstant were analyzed for cytokines like TNF-Alpha and IFN-Gamma.

In vitro studies *Mycobacterium* w when used along with lyphopolysaccharide (LPS) reduce LPS induced TNF/Alpha & also reduce IFN gamma secretion. The amount of inhibition seen is significant & is as good as basal level (complete inhibition).

EXAMPLE 2

Effect on LPS Induced Pyrexia

Figure 3:
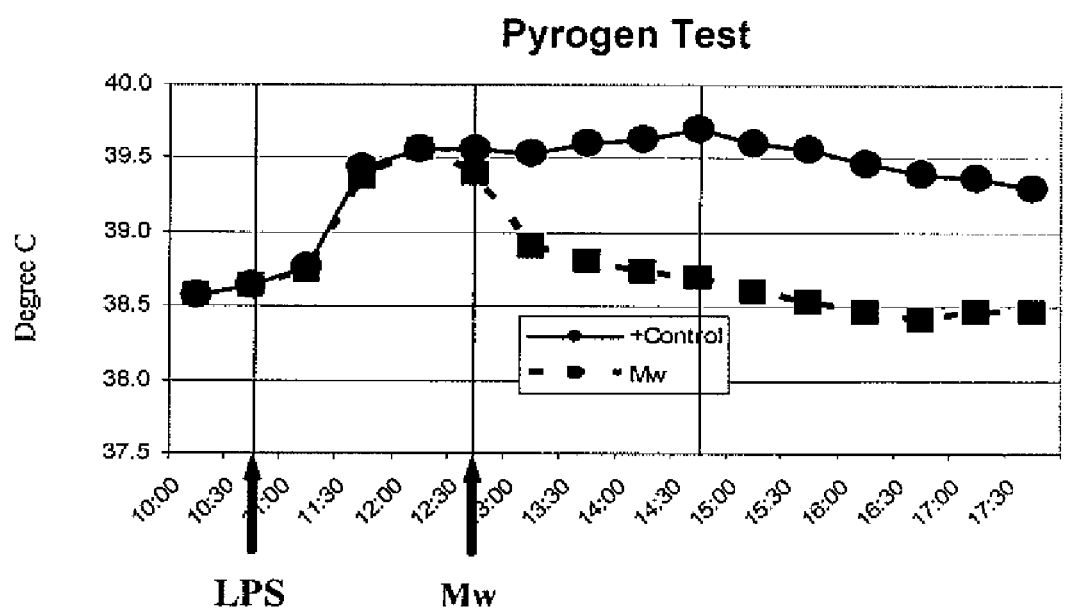

Rabbits were prepared as for pyrogen testing and temperature was monitored. Rabbits were administered intravenous injection of *E. coli*. lysate to mimic, endotoxin/lps induced pyrexia. Two hours later they were divided in to control arm and treatment arm. The treatment arm received injection of 2 ml of pharmaceutical composition containing heat killed *Mycobacterium* w $0.5 \times 10^9$ cell per 0.1 ml. The findings have been reproduced three times. Animals in treated group demonstrated lowering of temperature while control animals continued to have increased temperature. The effect persisted till the end of experiment is represented in FIG. 3.

Thus above examples demonstrate antagonist effect to effects of TLR ligands by pharmaceutical composition of present invention.

IV Examples Demonstrating Usefulness in Diseases wherein TLRs are Known to be over Expresses (A) Improved Survival in *E. coli* Induced Sepsis in Mice:

Injection of live—*E. coli* to mice by parenteral route results in sepsis with 100% mortality. The pharmaceuticals composition of present invention containing $0.5 \times 10^9$ cells of heat killed *Mycobacterium* w were evaluated in (Mw) for efficacy in this model of mice.

The animals were administered suspension of *E. coli* followed by *Mycobacterium* w by IV or ID route in various combinations with and without dexamethasone and amoxicillin. The highest improvement in survival is observed in animals treated with *mycobacterium* w along with the glucocorticoid and amoxicillin.

Experiment 1 (Intra peritoneal)

The mice were administered the 1 ml of live *E coli* (20 OD) intraperitoneally. The mice were treated with the different combination of amoxicillin (500 mG) and dexamehasone (2.0 mgm) therapies (FIG. 4). In each arm there were 10 animals. In control arm all animals died within 48 hrs (Group I). With interventions there was improved survival (Group II-VII). 100% survival was seen when Dexamethasone + Amoxicillin was combined with *Mycobacterium* w 0.1 ml delivered intradermally (Group IV). This was followed by same drugs but *Mycobacterium* w given intravenously (Group V). The results are graphically represented in FIG. 4.

Experiment 2 (Intra peritoneal)

In Second experiment the amoxicillin dose was reduced from 500mg/kg to 70 mg/kg (FIG. 5). Again best results were seen with *Mycobacterium* w given intradermally group II along with steroids and antibiotics followed by intravenous route group III. The results are graphically represented in FIG. 5.

Comparison of Experiment 1 & 2 reveals that amount of antibiotic is important. This is relevant clinically as sepsis is managed by massive dose of antibiotic and not conventional dose used for management of other infections.

Experiment 3 (Intravenous)

In third experiment the sepsis was induced by intravenous route and dexamethasone levels were reduced to 0.5 mg/kg from 2 mg/kg. The findings suggest that combination of steroids+antibiotics+*Mycobacterium* w (Group VII) provides improved survival. These three experiments showed that the use of *Mycobacterium* w improves survival in sepsis. The results are graphically represented in FIG. 4.

(B) *P. berghei* Model of Malaria:

The dysregulation of immune system in *P. Falciparum* malaria setting is known to induce sepsis-like syndromes. In animals infected with a fulminant form of malaria caused by *P. berghei* ANKA strain identical situation is seen. In a preliminary work done at IISc., Bangalore it is observed that *Mycobacterium* w+Artether administration results in 70% survival compared to 0% in control group receiving arteether or placebo only alone. Thus, *Mycobacterium* w has the capacity to reverse the sepsis-like syndromes caused in malaria infections.

Thus above examples (IV-A and IV-B) demonstrate usefulness of pharmaceutical composition of present invention in diseases in animals wherein TLRs are over expressed.

(C) Sepsis in Human

The lead product has been found useful in management of chronic infectious disease. It has also been found useful in resolution of steroid resistant granuloma, pleural effusion, hydro-pneumothorax, optic neuritis etc.

It has also been evaluated in management of sepsis.

EXAMPLE 1

In an elderly male patient aged 65 years with refractory Myeloma was found to be suffering from sepsis and was on ventilator for 6 weeks. He was receiving higher antibiotics (penems), EPO, GM CSF daily platelets transfusion for management. In spite of these, he was having a down hill course with progressive depletion of CD4 count. He was administered 0.2 ml of *Mycobacterium* w intradermally in two divided doses over deltoid. Within 48 hrs he was weaned off ventilator. He did not require any platelet infusion.

EXAMPLE 2

A fragile Young man with Old pulmonary TB developed bacterial infection of lung leading to sepsis. He was not responding to conventional therapy. He was administered *Mycobacterium* w 5 ml. I.V. for 5 days.

This resulted in cure from sepsis and infection leading to discharge from hospital. He was found to be stable without recurrence 6 weeks later. Both this examples suggests that *Mycobacterium* w is useful in management of sepsis in human (D) Optic Neuritis A 56 year old male patient with optic neuritis was found to have residual visual deficit following treatment with methyl prednisolone 1 gm intravenous daily for 3 days. The vision was stable at 6/36 and 6/18 respectively in right and left eye respectively. He was administered 5 ml of *Mycobacterium* w (prepared as per invention) in normal saline 500 ml intravenously agar infusion. The vision improved reached 6/12 and 6/9 respectively in right and left eye 10 days following initiation of treatment.

(E) Multiple Sclerosis

A 28 year old female patient had both lower limb paralyses due to (power grade 0) multiple sclerosis. This did not respond to therapy over 6 months. She did not receive any other therapy during the period.

She was administered 2 ml *Mycobacterium* w daily in 100 ml of normal saline intravenously for three days. She showed signs of recovery when evaluated 15 days later with power grade H in both lower limbs.

(F) Chronic Obstructive Pulmonary Disease

Use of pharmaceutical composition containing *Mycobacterium* w in management of chronic obstructive pulmonary disease results in decreased in secretions, decrease in rate of infection, decrease in number of exacubations requiring hospitalizations following examples demonstrates its effect on FEV1 and PEFR.

Experiment 1

Patients with chronic obstructive pulmonary disease were administered 0.1 ml of *Mycobacterium* w intradermally every fortnight for 2 months. This resulted in improvement in Forced expiration volume in one second (FEV1) by more than 50% in 5 of 9 patients it improved by more than 25% in rest. Improvement in peak expiratory flow rate (PEFR) also followed same pattern.

Experiment 2

In 16 patients with chronic pulmonary obstruction disease were administered $0.5 \times 10^9$ cells of heat killed *mycobacterium* w were administered intramuscularly after suspending them in 1 ml of normal saline.

Following single injection improvement in FEV1 was seen in 13 of 16 patients when examined following injection on day 15. (more than 50% 7, more than 25% 6). This improvement reached its peak by 4-6 weeks. Similarly improvement in PEFR was seen 11 of 16 patients.

Experiment 3

In 6 patients with chronic obstructive pulmonary disease $0.5 \times 10^9$ cells of heat killed *mycobacterium* w were delivered to nasal mucosa by nasal spray (0.1 ml). Improvement in FEV1 by more than 25% was seen in 5 of 6 patients with 3 achieving more than 50% improvement.

Improvement in PEFR by more than 25% was seen in 4 of 6 patients with 2 of them achieving more than 50% improvement.

Experiment 4

In ten patients with chronic obstructive pulmonary disease $0.5 \times 10^9$ cells of heat killed *mycobacterium* w suspended in 3 ml diluent were administered to the lung by nebulisation as a single administration. Improvement in FEV1 (more than 25%) was seen in all 10 patients.

The effect seems to persists for more than 6 weeks. The improvement in PEFR was more than 25% in 8 patients with 4 of them achieving more than 50% improvement.

(G) Multiple Myeloma

A 70 year old female with myeloma become refractory to conventional treatment and was having progression of disease. She had severe bone pain. The pain was so sever that she was unable to walk. *Mycobacterium* w was administered 0.1 ml of *Mycobacterium* w intradermally every month. The remission of disease was achieved. After three months of therapy she was symptom free and able to walk freely. Her hemoglobin improved from 5.5 gm % to 7.5 gm %.

Thus above examples (IV-C to IV-G) demonstrate positive effects of pharmaceutical composition of present invention in management of diseases in humans wherein TLRs are over expressed.

The examples (Example No 11-1 to 11'-3) illustrates, poly TLR antagonist activity of *mycobacterium* or its components when induced by known TLR agonist synthetic like CPG, ODN or naturally occurring like lipo-polysaccharide. The examples (Example No II-1 to 11-2) further illustrate antagonists' activity of *mycobacterium* w and its components to effects of TLR ligands like lipopolysaccharide, *E-coli*, etc. The examples (Example No IV-a, IV-b) further illustrate usefulness of *Mycobacterium* w or its components in management of diseases where in TLRs are over expressed. The examples (Example No IV-c, IV-d) further illustrates positive effects of *Mycobacterium* w or its components in management of disease like sepsis, optic neuritis, multiple sclerosis, chronic obstructive pulmonary disease, multiple myeloma.

REFERENCES

Akira Shimamoto, Albert J. Chong, Masaki Yada, Shin Shomura, Hiroo Takayama, Ani J. Fleisig, Matthew L. Agnew, Craig R. Hampton, Christine L. Rothnie, Denise J. Spring, Timothy H. Pohlman, Hideto Shimpo, and Edward D. Vernier, "Inhibition of Toll-like Receptor 4 With Eritoran Attenuates Myocardial Ischemia-Reperfusion Injury," Circulation, Vol. 114, (2006), I-270-I-274

Anders H J et al., "A Toll for lupus," *Lupus* Vol. 14(6), (2005), p 417-22

Anders H J, Zecher D, Pawar R D, Patole P S., "Molecular mechanisms of autoimmunity triggered by microbial infection," *Arthritis Res Ther*., Vol. 7(5), (2005), p 215-24

Angus, Derek C., Linde-Zwirble, Walter T.; Lidicker, Jeffrey, Clermont, Gilles, Crcillo, Joseph, Pinsky, Michael R., "Epidemiology of severe sepsis in the United States: Analysis of incidence, outcome, and associated costs of care," Critical Care Medicine. Vol. 29(7), (2001), p 1303-1310

Ann Marshak-Rothstein, "Toll-like receptors in systemic autoimmune disease," Nature Reviews Immunology, Vol. 6(11), (2006), p 823-35

Barrat, F. J. et al., "Nucleic acids of mammalian origin can act as endogenous ligands for Toll-like receptors and may promote systemic lupus erythematosus," J. Exp. Med. Vol. 202, (2005), p 1131-1139

Christ; William J., Rossignol; Daniel P., Kobayashi; Seiichi, Kawata; Tsutomu, (Eisai Co., Ltd.), "Substituted liposaccharides useful in the treatment and prevention of endotoxemia" U.S. Pat. No. 5,681,824 (Publication date: Oct. 28, 1997)

Donald N Cook, David S Pisetsky & David A Schwartz, "Toll-like receptors in the pathogenesis of human disease," Nature Immunology, Vol. 5(10), (2004), p 975-979

Emer Bourke, Daniela Bosisio, Jose'e Golay, Nadia Polentarutti, and Alberto Mantovani, "The toll-like receptor repertoire of human B lymphocytes: inducible and selective expression of TLR9 and TLR10 in normal and transformed cells," Blood. Vol. 102, (2003), p 956-963

Foo Y. Liew, Damo Xu, Elizabeth K. Brint and Luke A. J. O'neil, "Negative Regulation of Toll Like Receptor Mediated Immune Responses," Nature Reviews Immunology Vol. 5, (2005), p 446-458

Fumiko Nomura, Sachiko Akashi, Yoshimitsu Sakao, Shintaro Sato, Taro Kawai, Makoto Matsumoto, Kenji Nakanishi, Masao Kimoto, Kensuke Miyake, Kiyoshi Takeda, and Shizuo Akira, "Endotoxin Tolerance in Mouse Peritoneal Macrophages Correlates with Down-Regulation of Surface Toll-Like Receptor 4 Expression1," The Journal of Immunology, Vol. 164, (2000), p 3476-3479.

G Jego, R Bataille, A Geffroy-Luseau, G Descamps, C Pellat-Deceunynck, "Pathogen-associated molecular patterns are growth and survival factors for human myeloma cells through Toll-like receptors," Leukemia 20, (2006), p 1130-1137

Gewirtz A T, Vijay-Kumar M, Brant. S R, Duerr R H, Nicolae D L, Cho J H., "Dominant-negative TLR5 polymorphism reduces adaptive immune response to flagellin and negatively associates with Crohn's disease," Am J Physiol Gastrointest Liver Physiol. Vol. 290(6), (2006), pG 1157-63

Gilchrist M, Thorsson V, Li B, Rust A G, Korb M, Kennedy K, Hai T, Bolouri H, Aderem A., "Systems biology approaches identify ATF3 as a negative regulator of Toll-like receptor 4," Nature. Vol. 441(7090), (2006), p 173-8

Gowen B B, Hoopes J D, Wong M E I, Jung K H, Isakson K C, Alexopoulou L, Flavell R A, Sidwell R W, "TLR3 deletion limits mortality and disease severity due to Phlebovirus infection," J Immunol. Vol. 177(9), (2006), p 6301-7

Ishii Ken et al, "Toll gates for future immunotherapy," Current pharmaceuticals design, Vol. 12, (2006), p 4135-4142

J Bohnhorst, T Rasmussen, S H Moen, M FIÃ"ttum, L Knudsen, M BÃ"rset, T Espevik, A Sundan, "Toll-like receptors mediate proliferation and survival of multiple myeloma cells," Leukemia Vol. 20, (2006), p 1138-1144

Julianne Stack, Ismar R. Haga, Martina Schroder, Nathan W. Bartlett, Geraldine Maloney, Patrick C. Reading, Katherine A. Fitzgerald, Geoffrey L. Smith, and Andrew G. Bowie, "Vaccinia virus protein A46R targets multiple Toll-likeinterleukin-1 receptor adaptors and contributes to virulence," J. Exp. Med. Vol. 201(6), (2005), p 1007-1018

Ken J. Ishii, Satoshi Uematsu and Shizuo Akira, ."Toll-Gates for Future Immunotherapy," Current Pharmaceutical Design, Vol. 12, (2006), p 4135-4142

Leadbetter, E. A., Rifkin, I. R., Hohlbaum, A. M., Beaudette, B. C., Shlomchik, M. J., Marshak-Rothstein, A., "Chromatin-IgG complexes activate B cells by dual engagement of IgM and Toll-like receptors," Nature, Vol. 416, (2002), p 603-607.

Lene Malmgaard, Jesper Melchjorsen, Andrew G. Bowie, Søren C. Mogensen, and Soren R. Paludan, "Viral Activation of Macrophages through TLR-Dependent and -Independent Pathways1," The Journal of Immunology, Vol. 173, (2004), p 6890-6898

Lenert P S et al., "Targeting Toll-like receptor signaling in plasmacytoid dendritic cells and autoreactive B cells as a therapy for lupus."Arthritis Res Ther. Vol. 8(1), (2006), p 203

Liew, Foo Y.; Xu, Damo; Brint, Elizabeth K.; O'Neill, Luke A. J., "Negative regulation of Toll-like receptor-mediated immune responses," Nature Reviews Immunology, Vol. 5 (6), (2005), p 446-458

Maureen. Mullarkey, Jeffrey R. Rose, John Bristol, Tsutomu Kawata, Akufumi Kimura, Seiichi Kobayashi, Melinda Przetak, Jesse Chow, Fabian Gusovsky, William J. Christ and Daniel P. Rossignol, "Inhibition of Endotoxin Response by E5564, a Novel Toll-Like Receptor 4-Directed Endotoxin Antagonist," J Pharmaeol Exp. Thera., Vol. 304(3), (2003), p 1093-1102

Papadimitraki E D, Choulaki C, Koutala E, Bertsias G, Tsatsanis C, Gergianaki I, Raptopoulou A, Kritikos H D, Mamalaki C, Sidiropoulos P, Boumpas D T, "Expansion of toll-like receptor 9-expressing B cells in active systemic lupus erythematosus: implications for induction and maintenance of the autoimmune process,"Arthritis Rheum. Vol. 54(11), (2006), p 3601-11

R C Bone, R A Balk, F B Cerra, R P Dellinger, A M Fein, W A Knaus, R M Schein, and W J Sibbald, "Definitions for sepsis and organ failure and guidelines for the use of innovative therapies in sepsis," Chest Vol. 101, (1992), p 1644-55

Rossignol, D. P. & Lynn, M. TLR4 antagonists for endotoxemia and beyond, "TLR4 antagonist eritoran (E5564) and TAK-242 are found useful in management of sepsis," Curr. Opin. Investig. Drugs Vol. 6, (2005), p 496-502

Ruslan Medzhitov, Paula Preston-Hurlburt and Charles A. Janeway, Jr, "A human homologue of the Drosophila Toll protein signals activation of adaptive immunity," Nature Vol. 388, (1997), p 394-397

Shizuo Akira and Kiyoshi Takeda, "Toll-Like Receptor signaling," Nature Reviews Immunology Vol. 4, (2004), p 499

Subramanian S, Tus K, Li Q Z, Wang A, Tian X H, Zhou J, Liang C, Bartov G, McDaniel L D, Zhou X J, Schultz R A, Wakeland E K, "A TLR7 translocation accelerates systemic autoimmunity in murine lupus," Proc Natl Acad Sci USA. Vol. 103(26), (2006), p 9970-5

Sukkar M B, Xie S, Khorasani N M, Kon O M, Stanbridge R, Issa R, Chung K F, "Toll-like receptor 2, 3, and 4 expression and function in human airway smooth muscle," J Allergy Clin Immunol. Vol. 18(3), (2006), p 1641-8

Togbe D, Schnyder-Candrian S, Schnyder B, Couillin I, Maillet I, Bihl F, Malo D, Ryffel B, Quesniaux V F, "TLR4 gene dosage contributes to endotoxin-induced acute respiratory inflammation," J Leukoc Biol. Vol. 80(3), (2006), p 451-7

Toiyama Y, Araki T, Yoshiyama 5, Hiro J, Miki C, Kusunoki M., "The expression patterns of Toll-like receptors in the ileal pouch mucosa of postoperative ulcerative colitis patients," Surg Today. Vol. 36(3), (2006), p 287-90

Wang T, Town T, Alexopoulou L, Anderson J F, Fikrig E, Flavell R A, "Toll-like receptor 3 mediates West Nile virus entry into the brain causing lethal encephalitis," *Nat. Med.* Vol. 10(12), (2004), p 1366-73

Wei Jiang, Rui Sun, Haiming Wei, and Zhigang Tian, "Toll-like receptor 3 ligand attenuates LPS-induced liver injury by down-regulation of toll-like receptor 4 expression on macrophages," *PNAS*, Vol. 102(47), (2005), p 17077-17082

Xiong J, Zhu Z H, Liu J S, Wang Y, Wu H S., "The expression of toll-like receptor 2, 4 of livers in mice with systemic inflammatory response syndrome," *Hepatobiliary Pancreat Dis Int*. Vol. 5(1), (2006), p 143-6

We claim:

1. A method for treating sepsis, multiple sclerosis, or optic neuritis, characterized by over expression of a toll-like receptor (TLR), comprising administering to a patient in need thereof an effective amount of *Mycobacterium* w and/or constituents of *Mycobacterium* w.

2. The method according to claim 1, wherein the TLR is selected from TLR 3, 4, 5, 6, 7, 8 and 9.

3. The method according to claim 1, wherein the *Mycobacterium* w and/or constituents of *Mycobacterium* w reduce TLR activity.

4. The method according to claim 3, wherein the reduced TLR activity is induced by a TLR ligand.

5. The method according to claim 4, wherein the TLR ligand is selected from the group consisting of microorganisms, virus, virus like particles, lipopolysaccharides, endotoxin, CPG and ODN.

6. The method of claim 1, wherein said *Mycobacterium* w and/or constituents of *Mycobacterium* w is administered with dexamethasone or amoxicillin or a combination thereof.

7. The method of claim 1, wherein said *Mycobacterium* w and/or constituents of *Mycobacterium* w is administered without dexamethasone or amoxicillin a combination thereof.

* * * * *